United States Patent [19]

Cross et al.

[11] Patent Number: 5,013,865

[45] Date of Patent: May 7, 1991

[54] PROCESS FOR THE PREPARATION OF 2,4,6-TRIIODO-5-AMINO-N-ALKYLISOPHTHALAMIC ACID AND 2,4,6-TRIIODO-5-AMINO-ISOPHTHALAMIDE COMPOUNDS

[75] Inventors: Gregory D. Cross, Kansas City; Robert C. Chapman, Manchester, both of Mo.

[73] Assignee: Mallinckrodt, Inc., St. Louis, Mo.

[21] Appl. No.: 383,634

[22] Filed: Jul. 24, 1989

Related U.S. Application Data

[63] Continuation-in-part of Ser. No. 178,245, Apr. 6, 1988, abandoned.

[51] Int. Cl.$^5$ .................................... C07C 229/00
[52] U.S. Cl. .................................... 562/456; 560/37; 524/156
[58] Field of Search .................. 562/456; 560/37; 564/156

[56] References Cited

U.S. PATENT DOCUMENTS 3,145,197  8/1964  Hoey et al. .................... 260/211
4,396,598  8/1983  Lin ................................ 424/5

FOREIGN PATENT DOCUMENTS 616717  3/1961  Canada .
118225  7/1958  U.S.S.R. .

OTHER PUBLICATIONS

Singh et al., "Study on Radiopaque Iothalamic Acid—a Comparative Evaluation of its Synthesis", Chem. Abstracts, vol. 95, No. 15, Oct. 12, 1981, p. 631.
Dierbach et al., "Monomethyl Amide of 2,4,6-Triodo-5-Aminoisophthalic Acid", Chem. Abstracts, vol. 66, 1967, p. 2704.

*Primary Examiner*—Bruce Gray
*Attorney, Agent, or Firm*—Senniger, Powers, Leavitt & Roedel

[57] ABSTRACT

An improved process for preparing a compound selected from among 2,4,6-triiodo-5-amino-N-alkylisophthalamic acid, salts thereof, esters thereof, 2,4,6-triiodo-5-amino-isophthalamide, 2,4,6-triiodo-5-amino-N-hydroxyalkyl-isophthalamide and 2,4,6-triiodo-5-amino-N,N'-bishydroxyalkyl-isophthalamide. A substrate selected from among 5-amino-N-alkylisophthalamic acid, salts thereof, esters thereof 5-amino-isophthalamide, 5-amino-N-hydroxyalkyl-isophthalamide and 5-amino-N,N'-bishydroxyalkylisophthalamide is reacted with an iodine halide in an aqueous reaction medium. In accordance with the improvement, the substrate and a source of the iodine halide are added to the reaction medium at such relative rates that, at any instant substantially throughout the addition cycle, the substrate is present in stoichoimetric excess over the iodine halide, but the difference between the cumulative amount of the substrate that has been added to the medium at such instant, expressed as a proportion of the total ultimate charge of the substrate, and the cumulative amount of the source of iodine halide that has been added to the medium at such instant, expressed as a proportion of the total ultimate charge of the source of iodine halide, does not exceed 10%. When the substrate is 5-amino-isophthalamide, 5-amino-N-hydroxyalkyl-isophthalamide or 5-amino-N,N'-bishydroxyalkyl-isophthalamide, the cumulative amount of the iodine halide may be in stoichiometric excess of not more than about 10% of the substrate computed on the same basis.

Further improvements, respectively comprising incorporation of an alkaline buffer composition and operation at relative high dilution, are also disclosed.

49 Claims, No Drawings

PROCESS FOR THE PREPARATION OF 2,4,6-TRIIODO-5-AMINO-N-ALKYLISOPHTHALAMIC ACID AND 2,4,6-TRIIODO-5-AMINO-ISOPHTHALAMIDE COMPOUNDS

CROSS REFERENCE TO RELATED APPLICATION

This application is a continuation-in-part of application Ser. No. 178,245, filed Apr. 6, 1988 now abandoned.

BACKGROUND OF THE INVENTION

This invention relates to the synthesis of 2,4,6-triiodo-5-amino-N-alkylisophthalamic acid and 2,4,6-triiodo-5-amino-isophthalamide compounds, and more particularly, to an improved process for enhancing yields and improving the quality of the iodinated products.

2,4,6-triiodo-5-amino-N-alkylisophthalamic acid, or a salt or ester thereof, is a useful intermediate in the manufacture of X-ray contrast media. As described, for example, in Hoey U.S. Pat. No. 3,145,197, 5-acetamido-N-alkyl-2,4,6-triiodoiosphthalamic acid compounds are produced by treatment of 2,4,6-triiodo-5-amino-N-isophthalamic acid with an acylating agent such as a lower acyl halide or a lower alkanoic acid in the presence of a catalyst such as sulfuric acid or perchloric acid. In accordance with the scheme described in the Hoey patent, 5-nitroisophthalic acid is first converted to its dialkyl ester and one of the ester groups is then selectively hydrolyzed by careful treatment in a suitable solvent with one equivalent of a strong base such as sodium or potassium hydroxide. The monoester is reacted with a primary lower alkylamine to produce 5-nitro-N-alkylisophthalamic acid and the latter intermediate is subjected to catalytic hydrogenation to produce 5-amino-N-alkylisophthalamic acid commonly referred to as the "reduced half amide" or "RHA".

The RHA is triiodinated by reaction with a source of an iodine halide, preferably a source of iodine monochloride such as potassium iododichloride ($KICl_2$). In accordance with the Hoey process, the iodination reaction is effected with a modest net excess of iodinating agent, typically in hydrochloric acid solution. However, while the net overall charge of iodinating agent is in excess, the Hoey process involves first charging all or a substantial portion of the RHA to an aqueous reaction medium, and then adding the iodinating agent over a period of time. Thus, throughout most of the reaction period, there is a substantial excess of RHA in the reaction zone. In one embodiment described by Hoey, the entire RHA charge is first dissolved in a hydrochloric acid medium and the iodinating agent thereafter added thereto. In another embodiment, RHA is first reacted with less than a stoichiometrically equivalent amount of potassium iododichloride in aqueous suspension and, after several hours, sodium hydroxide and the remainder of the potassium iododichloride are added and reaction carried to completion.

The product of the reaction has generally been found to contain a fraction of mono- and di-iodinated species, thereby detracting from both product yield and product quality.

Because the RHA is typically dissolved in a hydrochloric acid medium preparatory to the addition of the iodinating agent, and because hydrochloric or other hydrogen halide acid is, in any event, a product of the reaction, the methods previously known to the art have involved conducting at least a substantial portion of the reaction at acid concentrations sufficiently high that the pH of the reaction medium is negative. Such pH conditions inhibit the progress of the reaction, thus requiring the use of an ultimate excess of the iodine halide source to drive the reaction to completion. Since the iodine halide source is not practicably recoverable from the reaction medium, the excess is effectively lost, with a resultant adverse impact on manufacturing cost. Moreover, even with an excess of iodinating reagent, the reaction is not always driven fully to completion so that the quality of the product may be less than desired.

As the reaction between RHA and iodinating agent progresses, the iodinated product compound precipitates from the reaction mixture as a crystalline solid. Acidification at the end of the reaction period precipitates the triiodo product remaining in solution. This product is recovered from the reaction mass by filtration or centrifugation. The purity of iodinated reaction product and yield obtained thereof are dependent on the efficiency of this separation. In the conventional process, some difficulty has been experienced with effective separation of the product crystals from the reaction medium mother liquor. This has detracted from the yield commercially achievable in the manufacture of X-ray contrast media from the 2,4,6-triiodo-5-amino-N-alkylisophthalamic acid produced by iodination of RHA.

Similarly, the compound 5-amino-N,N'-bis(2,3-dihydroxy-propyl)-2,4,6-triiodoisophthalamide is an intermediate in the preparation of N,N'-bis(2,3-dihydroxypropyl)-5[N-(2-hydroxyethyl)glycolamido]-2,4,6-triiodoisophthalamide. The latter compound is a nonionic x-ray contrast agent (see Lin U.S. Pat. No. 4,396,598).

Heretofore, it has been known to prepare 5-amino-N,N'-bis(2,3-dihydroxypropyl)-2,4,6-triiodoisophthalamide from 5-amino-N,N'-bis(2,3-dihydroxypropyl)isophthalamide (known as the "reduced diamide") by acidifying an aqueous reaction medium containing the latter compound with 30% hydrochloric acid to a pH of 0.9–1.0, heating the resulting solution to a temperature of approximately 81°–84° C. and adding an iodine monochloride aqueous solution over a period of ¾ to 1 hour. The solution is then stirred and heated at a temperature of 81°–84° C. for 3 to 4 hours. After the reaction is completed, the solution is cooled to 55°–60° C. and sodium bisulfite is added to destroy excess iodine and/or iodine monochloride. The solution is then cooled to approximately 25° C. and sodium hydroxide solution is added slowly at 25°–40° C. to adjust the pH to 4–7. After seeding with 5-amino-N,N'-bis(2,3-dihydroxypropyl)-2,4,6-triiodoisopthalamide, the solution is cooled to 0°–5° C. and stirred to effect precipitation of the desired product, 5-amino-N,N'-bis(2,3-dihydroxypropyl)-2,4,6-triiodoisophthalamide.

The above-described process suffers from certain shortcomings. It undesirably produces a product containing impurities which may be hydrolysis products and also containing a small amount of uniodinated reduced amide. Moreover, the reaction between the reduced amide and iodine monochloride produces so much HCl that the pH of the reaction medium falls below 0 and undesirably retards the desired reaction and reduces the yield of the desired product.

There has been a need in the art for an improved process which affords improved yields and produces a higher purity 2,4,6-triiodo-5-amino-N-alkylisophthalamic acid product or 5-amino-N,N'-bis(2,3-dihydroxypropyl)-2,4,6-triiodoisophthalamide or other 2,4,6-triiodo-5-aminoisophthalamide compound.

SUMMARY OF THE INVENTION

Among the several objects of the present invention, therefore, may be noted the provision of an improved process for the preparation of 2,4,6-triiodo-5-amino-N-alkylisophthalamic acid or 2,4,6-triiodo-5-amino-isophthalamide compound; the provision of such a process which affords improved yields; the provision of such a process which provides products of enhanced quality; the provision of a process which provides favorable kinetics and improved productivity; and the provision of a process which facilitates manufacture of 2,4,6-triiodo-5-amino-N-alkylisophthalamic acid or 2,4,6-triiodo-5-amino-isophthalamide compound, and the X-ray contrast media for which they are intermediates, at relatively low manufacturing cost.

Briefly, therefore, the present invention is directed to an improvement in a process for the preparation of an iodinated product compound selected from among 2,4,6-triiodo-5-amino-N-alkylisophthalamic acid, salts thereof, esters thereof, 2,4,6-triiodo-5-amino-isophthalamide, 2,4,6-triiodo-5-amino-N-hydroxyalkyl-isophthalamide and 2,4,6-triiodo-5-amino-N,N'bishydroxyalkyl-isophthalamide. The process comprises reaction of a substrate selected from among 5-amino-N-alkylisophthalamic acid, salts thereof, esters thereof, 5-aminoisophthalamide, 5-amino-N-hydroxyalkyl-isophthalamide and 5-amino-N,N'-bishydroxyalkyl-isophthalamide, with an iodine halide in an aqueous reaction medium. According to the improvement, the substrate and a source of the iodine halide are added to the reaction medium at such respective rates that, at any instant during the addition cycle, the substrate is present in stoichiometric excess over the iodine halide, but the arithmetic difference between the cumulative amount of the substrate that has been added to the medium at said instant, expressed as a proportion of the total ultimate charge of the substrate, and the cumulative amount of the source of iodine halide that has been added to the medium at said instant, expressed as a proportion of the total ultimate charge of iodine halide source, does not exceed about 10%. In further accordance with the improvement, when the substrate is 5-amino-isophthalamide, 5-amino-N-hydroxyalkyl-isophthalamide or 5-amino-N,N'-bishydroxyalkyl-isophthalamide, the cumulative amount of the iodine halide may be in stoichiometric excess of not more than about 10% over the substrate, computed on the same basis.

The present invention is further directed to an improvement in the aforesaid process, in accordance with which the reaction is carried out in the presence of an alkaline buffer composition. The proportion of the alkaline buffer composition is sufficient that the pH of the reaction medium is maintained between about 0 and about 2 during the course of the reaction.

The invention further includes an improvement in the aforesaid process, in accordance with which a sufficient proportion of water is maintained in the reaction medium so that the concentration of the iodinated product compound does not exceed about 0.08 moles/liter in the reaction mass at the conclusion of the iodination reaction, the reaction mass comprising the combination of the liquid phase comprising said reaction medium and any solids that precipitate during the course of the reaction.

More particularly, the invention comprises a process for the preparation of an iodinated compound selected from among 2,4,6-triiodo-5-amino-N-alkylisophthalamic acid, salts thereof, and esters thereof. The process comprises adding to a reaction vessel an aqueous substrate solution and an aqueous iodine halide charge solution, the substrate solution containing a substrate selected from among 5-amino-N-alkylisophthalamic acid, salts thereof, and esters thereof, and said iodine halide charge solution containing a source of iodine halide. The substrate is reacted with the source of iodine halide in an aqueous medium in the reaction vessel to produce an iodinated compound. The respective rates of addition of the substrate solution and iodine halide charge solution to the vessel are such that, at any instant substantially throughout the addition cycle, the substrate is present in excess over the iodine halide, but the arithmetic difference between the cumulative amount of substrate that has been added to said medium at such instant, expressed as a proportion of the total ultimate charge of the substrate, and the cumulative amount of the iodine halide source that has been added to the medium at such instant, expressed as a proportion of the total ultimate charge of the source of iodine halide, does not exceed about 10%. Reaction is carried out in the presence of an alkaline buffer composition, the proportion of the alkaline buffer composition being sufficient so that the pH of the reaction medium is maintained between about 0 and about 3 during the course of the reaction. The pH of the reaction medium at the beginning of the reaction is between about 2.5 and about 3.0. The concentration of the iodinated product compound does not exceed about 0.08 moles/liter in the reaction mass at the conclusion of the iodination reaction. The reaction mass comprises the combination of a liquid phase comprising the reaction medium and any solids precipitated from the medium during the course of the reaction.

Also, more particularly, the invention comprises a process for the preparation of 5-amino-N,N'-bis(2,3-dihydroxypropyl)-2,4-6-triiodoisophthalamide. The process comprises the simultaneous coaddition to an aqueous reaction medium of an aqueous solution containing 5-amino-N,N'-bis(2,3-dihydroxypropyl)isophthalamide and an alkaline buffer composition and an aqueous solution of iodine monochloride, the aqueous reaction medium being maintained at a temperature within the range 75°–85° C. and at a pH within the range 0.5 to 2.5 during the simultaneous coaddition, and continuing the simultaneous coaddition for a period of approximately 2 to 2.5 hours.

Other objects and features will be in part apparent and in part pointed out hereinafter.

DESCRIPTIoN OF THE PREFERRED EMBODIMENTS

In accordance with the present invention, it has been found that limiting the unreacted RHA or diamide content of the iodination reaction system promotes conversion of that substrate to its 2,4,6-triiodo species, thereby minimizing the mono and di-iodo species in the final reaction mixture and enhancing the yield realized in the process. Moreover, it has been demonstrated that this improvement in conversion to the triiodo species is achieved without any significant increase in the formation of azo compound by products. Additionally, it has been found that, by maintaining the instantaneous excess of RHA below about 10%, high conversion to 2,4,6-triiodo-5-amino-N-alkylisophthalamic acid is achieved without a significant ultimate net excess of iodine halide. Thus, for example, by simultaneously adding substrate and iodine halide to an aqueous reaction medium at such respective rates that the instantaneous excess of RHA or diamide never exceeds about 10%, the reaction may be driven essentially to completion by the ultimate addition of a cumulative excess of iodine halide over RHA or diamide of only about 1%.

Several slightly varying computations may be used to determine the instantaneous excess of RHA or diamide. For example, the instantaneous excess of RHA or diamide may be considered as the difference, at any instant substantially throughout the addition cycle, between the cumulative number of equivalents of RHA or diamide that have been added to the reaction medium at that instant vs. the cumulative number of equivalents of iodine halide source that have been added to the reaction medium at that instant, expressed as a proportion of the total ultimate charge of iodine halide source over the addition cycle. However, since the total ultimate reactor charges of RHA or diamide and iodine halide source are generally equivalent stoichiometrically, the instantaneous excess of RHA or diamide is preferably defined by the arithmetic difference between the cumulative amount of RHA or diamide that has been delivered to the reactor at a given instant, expressed as a proportion of the total ultimate RHA or diamide charge, and the cumulative amount of iodine halide source that has been delivered at that instant, expressed as a proportion of the total ultimate iodine halide charge.

Whichever basis of computation is used, the instantaneous excess of RHA or diamide should fall in the range of between 0 and about 10%, preferably between about 2% and about 10%. This result is achieved by simultaneous addition (coaddition) of the reactants to the reaction medium and carefully monitoring the proportion of each reactant charged (or the net excess of RHA or diamide present in the medium), either on a continuous basis, or at frequent discrete intervals of time. It will be understood, of course, that where the ultimate charges of RHA or diamide and ICl are essentially equivalent, as is the case in the preferred embodiments of the process of the invention, a 2-10% RHA or diamide excess cannot be maintained entirely throughout the addition period. However, the desired excess may be maintained through substantially the entire period by, for example, stretching out the ICl addition for 5 to 10 minutes longer than the RHA or diamide addition, and maintaining the 2-10% excess until that last 5-10 minutes.

The improved process of the invention is applicable to the preparation of 2,4,6-triiodo-5-amino-N-alkylisophthalamic acid compounds such as 2,4,6-triiodo-5-amino-N-methylisophthalamic acid and to the preparation of 2,4,6-triiodo-5-amino-isophthalamide compounds such as 2,4,6-triiodo-5-amino-N-hydroxymethyl-isophthalamide and 2,4,6-triiodo-5-amino-bis(2,3-dihydroxypropyl)isophthalamide. When the substrate is a 5-amino-isophthalamide, 5-amino-N-hydroxyalkyl-isophthalamide or 5-amino-N,N'-bishydroxyalkyl-isophthalamide compound, then the excess of the diamide substrate over iodine halide is maintained below about 10% as described above or, alternatively, the cumulative amount of the iodine halide may be in stoichiometric excess of not more than about 10% over the diamide substrate, computed on the same basis described in detail above, i.e. the instantaneous excess of iodine halide over the diamide substrate may be in the range of between 0 and about 10% on the above-noted computational basis.

When the reaction is carried out by coaddition of reactants, the amount of hydrochloric acid charged to the reaction medium can be minimized, thereby reducing the usage of this raw material. Minimizing the amount of the HCl charge also contributes to control of the reaction pH at a level above 0, thus enhancing the kinetics of the iodination reaction and helping to drive it to completion even in the absence of any significant net ultimate excess of iodine halide. Thus, it has been found that, when the reaction is carried out by coaddition as described above, the amount of HCl added to the system can be limited to that sufficient to establish an initial pH of no greater than about 3 in the reaction system. During the reaction, acid is preferably not added to the reaction system. The pH is preferably adjusted to about 0.3 to 0.7 after the completion of the reaction to facilitate separation of the iodinated product by crystallization. Typically, a small amount of HCl is added for this purpose.

It has further been discovered that iodination of a substrate comprising an 5-amino-N-alkylisophthalamic acid (RHA), or its esters or salts, or 5-amino-isophthalamide, 5-amino-N-hydroxyalkyl-isophthalamide or 5-amino-N,N'-bishydroxyalkyl-isophthalamide (reduced diamide), is promoted by the presence of an alkaline buffer composition in the reaction medium. Hydrogen halide, produced as a byproduct of the reaction of an iodine halide with the substrate, is neutralized by the buffer, thereby maintaining the pH of the reaction medium at between about 0 and about 2. Control of the pH in this range essentially eliminates the inhibitory effect otherwise caused by the generation of HCl or other hydrogen halide during the reaction. When the pH is maintained in the 0 to 2 range, enhancement of the reaction kinetics is sufficient that the triiodination reaction can be carried fully to completion without the necessity of using any stoichiometric excess of the source of iodine monohalide. Because the reaction is brought to completion, the product is substantially free of partially iodinated intermediates, and thus product quality is further improved. In turn, the products if this invention may be converted to commercially valuable X-ray contrast media in accordance with the process of the aforesaid Hoey or Lin patents, and the superior quality of the iodinated RHA or diamide intermediate conduces to enhanced quality of the contrast media product as well.

Improved kinetics of reaction also allows a shortened iodination batch cycle, with consequent gain in productivity. An incremental gain in reaction rate is achieved through the reduction in HCl charge associated with the coaddition of RHA or diamide and iodinating agent. However, by itself, coaddition does not eliminate the need for at least a slight net excess of iodinating agent in the total ultimate charge of reactants to the reaction vessel. By control of pH in the 0-2 range with an alkaline buffer, the excess of iodinating agent may be essentially eliminated, and the reaction driven to completion in a reasonably short batch cycle at a temperature of 75°-85° C. Increased productivity and reduced consumption of iodinating reagent provide significant economies in the manufacturing cost of the triiodo intermediate and the final X-ray contrast media products.

Preferably, the alkaline buffer composition is an alkali metal acetate such as sodium acetate. However, amonium hydroxide as well as a variety of inorganic salts of strong bases and weak acids can be used. For example, the alkaline buffer composition may comprise an alkali metal salt of phosphoric acid or an alkali metal salt of citric acid. Alkali metal salts of propionic and other alkanoic acids may also be used, but these are less preferred because of their relatively high cost. Whatever alkaline buffer composition is used, it is incorporated in the reaction medium in a proportion sufficient to maintain the pH of the reaction medium between about 0 and about 3 during the course of the iodination reaction.

Ammonium hydroxide has been found highly effective in decreasing the digest period for the reaction to go to completion. For instance, by providing two discrete pH adjustments with ammonium hydroxide during coaddition of substrate and idine halide, the reaction may be brought to completion in 4 hours at 80° C. Incorporation of sodim acetate allows the pH to be maintained in the 1-2.5 range throughout the addition of reactants, and permits the reaction to be completed in 3 hours. 98.5% purity iodinated product is obtained from the reaction.

The iodinating reagent is iodine chloride or another iodine halide. Typically an iodine halide source is provided by adding both molecular iodine and another molecular halogen to an alkali metal halide solution. Thus, for example, molecular iodine and chlorine gas may be added to a solution of sodium chloride or potassium chloride, yielding either sodium iododichloride or potassium iododichloride, each of which is a source of iodine monochloride. Preparation of $NaICl_2$ or $KICl_2$ in this fashion is well known to those skilled in the art.

In carrying out the preferred process of the invention for the preparation of 2,4,6-triiodo-5-amino-N-alkylisophthalamic acid compounds, and aqueous substrate solution containing 5-amino-N-alkylisophthalamic acid and an aqueous iodine halide solution are added simultaneously to an aqueous reaction medium in a reaction vessel provided with an agitator. The aqueous reaction medium may be established simply by the initial mixing of the two reactant solutions, after which the process proceeds by continued coaddition to that medium. Preferably, however, an initial charge of water, or of an acidified solution of RHA, is introduced into the reaction vessel to establish the aqueous medium before coaddition commences. If the initial charge is distilled water, addition of the iodinating agent charge solution is begun just slightly ahead of the addition of substrate charge solution so as to be certain that the RHA is not exposed to a pH above about 3. If the initial charge is an acidified RHA solution, the amount of the initial charge is controlled so that it does not contain more than about 10% of the total ultimate RHA charge. Conveniently, the substrate solution contains between about 0.02 and about 2 moles per liter of RHA and the iodine halide solution contains between about 0.05 and about 5 moles per liter of iodine halide or source thereof. At standard dilutions, the substrate charge solution may typically contain 0.1-0.3 moles/liter RHA, and the iodine halide charge solution may typically contain 0.2-0.5 equivalents/liter iodine halide source.

Where an initial water charge or RHA solution is introduced into a reaction vessel, this initial charge is preferably heated to an elevated temperature, for example in the range of 50° to 80° C. before coaddition begins. Thereafter simultaneous introduction of the substrate solution and iodine halide solution to the reaction vessel is carried out and completed over a period of about 1 hour, during which the contents of the vessel are stirred to produce a homogeneous charge mixture. Agitation is continued and this mixture is maintained at an elevated temperature, typically in the range of 75° to 100° C., to complete the reaction.

The alkaline buffer composition may be introduced into the reaction medium either prior to or simultaneously with the introduction of reactant solutions. Preferably, however, the buffer composition is premixed with the substrate charge solution before it is mixed with the iodine halide solution.

Where the alkaline buffer composition is an alkali metal acetate, it is preferably prepared in situ by simultaneously adding glacial acetic acid and an aqueous solution of alkali metal hydroxide to the reaction medium or to the substrate charge solution. Preferably, the alkali metal hydroxide solution has a strength of between about 25% and about 70% by weight, most preferably about 50% by weight, alkali metal hydroxide. In situ preparation of the alkali metal acetate in this fashion facilitates plant operations since both alkali metal hydroxide solutions and glacial acetic acid are readily available liquid materials which are easily handled, thereby avoiding the necessity of mixing solid alkali metal acetate with other liquid process materials.

As the iodination reaction progresses, product 2,4,6-triiodo-5-amino-N-alkylisophthalamic acid is precipitated from the aqueous reaction mixture. The progress of the reaction may be followed by analysis of samples, preferably by high pressure liquid chromatography. At the conclusion of the reaction, an alkali metal bisulfite or other halogen scavenger is added to quench any free iodine halide remaining in the system, after which the reaction mixture is cooled and adjusted to pH of about 0.5 by addition of hydrochloric acid. Hydrochloric acid addition effects precipitation of residual product from the aqueous phase. Thereafter the reaction mixture is filtered or centrifuged for recovery of product, and the filter or centrifuge cake is washed with water and dried.

It has been found that the separation of iodinated product compound crystals from the acidified reaction medium is significantly improved if the reaction is run in a relatively dilute system. In accordance with the conventional process, the the total amount of RHA added to the reaction medium has been typically equivalent to a concentration of 0.05 to 0.15 moles per liter final reaction mass, while the amount of ICl added has been equivalent to a concentration in the neighborhood of 0.15–0.75 moles per liter, thereby resulting in the production of 2,4,6-triiodo-5-amino-N-alkylisophthalamic acid at a concentration in the range of 0.05 to 0.15 moles per liter in the slurry reaction mass. In accordance with the present invention, it has been discovered that separation is substantially facilitated, and the purity of the resultant crystalline product enhanced, if the iodinated product compound is produced in a concentration of between about 0.02 and about 0.04 moles per liter. This result may be achieved either through the use of relatively dilute reactant solutions, e.g., a substrate solution having a concentration of between about 0.02 and about 0.08, preferably about 0.02 to about 0.04, moles per liter and an iodinating agent solution having an iodine halide source concentration of between about 0.05 and about 0.1 moles per liter, or by introducing a substantial initial charge of water into the reaction vessel before the addition of reactant solutions is commenced. In either case the sum of the amounts of substrate and iodinated product preferably does not exceed about 0.08 moles/liter in the reaction mixture at any time during the cycle.

In carrying out the preferred process of the invention for the preparation of 2,4,6-triiodo-5-aminoisophthalamide, 2,4,6-triiodo-5-amino-N-hydroxyalkyl-isophthalamide and 2,4,6-triiodo-5-amino-N,N'-bishydroxyalkyl-isophthalamide compounds such as 5-amino-N,N'-bis (2,3-dihydroxypropyl)-2,4,6-triiodoisophthalamide, an aqueous solution containing 5-amino-N,N'-bis(2,3-dihydroxypropy))isophthalamide (reduced diamide) and an alkaline buffer composition and an aqueous iodine halide solution are added simultaneously to an aqueous reaction medium in a reaction vessel provided with an agitator. This simultaneous coaddition of the reactants preferably occurs over a period of 2 to 2.5 hours and the aqueous reaction medium is preferably maintained at a temperature within the range 75° to 85° C. and at a pH within the range 0.5 to 2.5 during the simultaneous coaddition. The rates of addition of the reduced diamide and iodine halide reactants are regulated so that the stoichiometric excess of one over the other does not exceed the upper limit of about 10% as previously described. To avoid diminishing the reaction rate of the desired iodination reaction, the temperature is preferably not allowed to fall below about 75° C.

As the iodination reaction progresses, the formation of the product (e.g. 5-amino-N,N'-bis(2,3-dihydroxypropyl)-2,4,6-triiodoisophthalamide) may be followed by analysis of samples as by high performance liquid chromatography. Upon completion of the reaction, the reaction mixture is treated with an alkali metal bisulfite (e.g. sodium bisulfite) or other halogen scavenger to destroy excess iodine or iodine halide remaining in the system. The reaction medium is then cooled, the pH adjusted to 4–7 and the medium seeded with the desired product (e.g. 5-amino-N,N'-bis(2,3-dihydroxypropyl)-2,4,6-triiodoisophthalamide) to precipitate the iodinated product.

In utilizing the improved process of the invention for the preparation of 2,4,6-triiodo-5-amino-isohphthalamide compounds such as 5-amino-N,N'-bis(2,3-dihydroxypropyl)-2,4,6-triiodoisophthalamide, it has been found that faster crystallization and improved filterability of the desired end product are achieved with the product being obtained in higher yield and with fewer impurities.

The following examples illustrate the invention.

EXAMPLE 1

An RHA charge solution was prepared by adding glacial acetic acid (29 ml) and a 35°Be' sodium hydroxide solution (50 ml) to a 0.1536 gpl solution of 5-amino-N-methylisophthalamic acid (260 ml; 0.617 mole RHA). The pH of the RHA charge solution was 6.5 and the total volume was 380 ml.

Water (1193 ml) was charged to a stirred tank reaction vessel and heated therein to a temperature of 74° C. Thereafter about 7.5% of the RHA charge solution (i.e., about 28.5 ml) was added to the reaction vessel, followed by an amount of hydrochloric acid sufficient to adjust the pH in the vessel to 1.55. After addition of HCl, the remainder of the RHA charge solution and an iodine monochloride charge solution (0.356 gpl ICl in NaCl solution; 285 ml; 0.625 moles ICl) were added simultaneously to the reaction vessel over a period of about 2 hours. The schedule of coaddition of charge solutions and the pH of the contents of the reaction vessel during the course of the addition are set forth in Table 1. After addition of the charge solutions was completed, the resulting mixture was heated under agitation for 3 hours, after which the pH was 0.97. The reaction mixture was cooled to 65° C. and sodium bisulfite (1.6 g) was added thereto. The bisulfite treated reaction mixture was cooled to 40° C. and the pH was adjusted to 0.5 with 37% HCl. Precipitated product 2,4,6-triiodo-5-amino-N-methyl-isophthalamic acid was recovered by filtration. The cake was washed with water (200 ml) and dried in an oven at 95° C. for three days. Yield was 114.29 g.

TABLE 1

| Time | RHA left (ml) | % RHA remaining to be added | ICl Remaining to be added (ml) | % ICl left to be added | % difference | pH |
|---|---|---|---|---|---|---|
| 8:45 | 351.5 | 92.5 | 285 | 100 | 7.5 | 1.55 |
| 8:50 | 335 | 88.16 | 272 | 95.44 | 7.28 | 1.45 |
| 9:00 | 304 | 80 | 246 | 86.32 | 6.32 | 1.32 |
| 9:05 | 285 | 75 | 233 | 81.75 | 6.75 | 1.30 |
| 9:10 | 270 | 71.1 | 220 | 77.19 | 6.09 | 1.34 |
| 9:21 | 236 | 62.11 | 196 | 68.77 | 6.66 | 1.40 |
| 9:30 | 206 | 54.01 | 174 | 61.05 | 6.84 | 1.38 |
| 9:40 | 178 | 46.84 | 153 | 53.68 | 6.84 | 1.43 |
| 9:50 | 145 | 38.16 | 132 | 46.32 | 8.16 | 1.48 |
| 10:00 | 115 | 30.26 | 107 | 37.54 | 7.28 | 1.47 |
| 10:10 | 83 | 21.48 | 85 | 29.82 | 7.98 | 1.48 |
| 10:20 | 52 | 13.68 | 64 | 20.46 | 8.78 | 1.50 |
| 10:30 | 20 | 5.26 | 39 | 13.68 | 8.42 | 1.50 |
| 10:40 | | | | | 7.50 | |
| 10:50 | addition complete | | | | | |

EXAMPLE 2

2,4,6-triiodo-5-amino-N-methylisophthalamic acid was prepared generally in accordance with the procedure described in Example 1. In the preparation of this example, 0.1536 gpl RHA charge solution (260 ml; 0.617 mole RHA) and 0.356 gpl iodine monochloride charge solution (281.43 ml; 0.617 mole ICl) were utilized. The schedule of simultaneous charge solution addition is set forth in Table 2. After addition of charge solutions, the resulting mixture was heated at 90° C. for three hours and then cooled to 75° C. Sodium bisulfite (1.25 g) was added to the cooled reaction mixture, after which the pH was 1.12. After bisulfite treatment of the reaction solution, 37% HCl solution was added thereto to a pH of 0.52. Dry weight of the recovered product was 114.5 g. Analysis of the product by high pressure liquid chromatography (HPLC) indicated that the product contained 97.41% 2,4,6-triido-5-amino-N-methylisophthalamic acid, 0.214% of diiodo species and 1.75% of monoiodo species.

TABLE 2

| Time | mls RHA left to be added | % RHA left to be added | ml ICl left to be added (ml) | % ICl left to be added | % difference | pH |
|---|---|---|---|---|---|---|
|  | 351.5 | 92.5 | 0 | 100 | 7.5 | 1.49 |
| 9:05 | 340 | 89.47 | 270 | 96.43 | 6.96 | 1.47 |
| 9:10 | 325 | 85.53 | 261.4 | 92.89 | 7.36 | 1.41 |
| 9:20 | 304 | 80 | 246 | 87.41 | 7.41 | 1.37 |
| ppt. starting at 9:20 | | | | | | |
| 9:25 | 287 | 75.5 | 236 | 83.86 | 8.33 | 1.42 |
| 9:35 | 264 | 69.47 | 218 | 77.46 | 7.99 | 1.46 |
| 9:40 | 247 | 65 | 208 | 73.91 | 8.91 | 1.52 |
| 9:50 | 223 | 58.68 | 189 | 67.16 | 8.48 | 1.49 |

TABLE 2-continued

| Time | mls RHA left to be added | % RHA left to be added | ml ICl left to be added (ml) | % ICl left to be added | % difference | pH |
|---|---|---|---|---|---|---|
| 10:00 | 200 | 52.63 | 169 | 60.05 | 7.42 | 1.42 |
| 10:10 | 170 | 44.74 | 150 | 53.30 | 8.50 | 1.53 |
| 10:25 | 133 | 35 | 122 | 43.35 | 8.35 | 1.58 |
| 10:35 | 107 | 28.16 | 103 | 36.60 | 8.44 | 1.58 |
| 10:50 | 67 | 17.63 | 75 | 26.65 | 9.02 | 1.68 |
|  | 67 | 17.63 | 70 | 24.87 | 7.24 | 1.54 |
| 11:00 | 44 | 11.58 | 55 | 19.54 | 7.96 | 1.64 |
| 11:15 | — | 0 |  |  |  | 1.60 |
| 11:20 |  |  |  | 0 |  | 1.14 |
| 11:40 | T @ 92° C. |  |  |  |  |  |

EXAMPLE 3

2,4,6-triiodo-5-amino-N-methylisophthalamic acid was prepared generally in accordance with the procedure described in Example 2. In the example, however, the initial water charge to the reaction vessel was 1100 ml and the water was heated to 85° C. before addition of charge solutions was commenced. RHA charge solution (7.5% of total; 28.5 ml) was then charged and 37% HCl added to a pH of 1.48. Next, a portion of the iodine monochloride solution (7.5% of total; 20 ml) was added and the resulting mixture was agitated at 85° C. for 10-15 minutes, after which crystallization had begun. Simultaneous RHA and ICl charge solution addition was then carried out in accordance with the schedule set forth in Table 3. After coaddition of charge solutions was completed, the resulting mixture was heated to 92° C. and maintained at that temperature for three hours. The reaction solution was then cooled to 75° C. and sodium bisulfite (0.89 g) was added. After bisulfite treatment, the solution was cooled to 35°-40° C. and the pH adjusted to 0.49 by addition of 37% HCl (35 ml). The pH was subsequently observed to rise to about 0.6, and another portion of 37% HCl (15 ml) was added to bring the pH down to 0.5. The crystalline precipitate product was recovered by filtration, and the cake was washed with water (200 ml) and dried at 95° C. over a weekend. The dry weight of the product was 113.84. Analysis of the product by HPLC indicated that it contained 97.76% by weight 2,4,6-triido-5-amino-N-methylisophthalamic acid, 1.13% by weight monoiodo species, and 0.27% by weight diiodo species.

TABLE 3

| Time | RHA left (ml) | % RHA left | ICl left to be added (ml) | % ICl left to be added | % difference | pH |
|---|---|---|---|---|---|---|
|  | 351.5 | 92.5 | 281.43 | 100 | 7.5 | 1.48 |
|  | 7.5 — 37% HCl |  |  |  |  |  |
| 9:13 | 351.5 | 92.5 | 261.43 | 92.89 | .39 | .97 |
| 9:20 | started ppt. |  |  |  |  |  |
| 9:25 | started RHA/ICl to maintain 3.5%-4% RHA excess. |  |  |  |  |  |
| 9:36 | 322 | 84.74 | 250 | 88.83 | 4.09 | 1.11 |
| 9:43 | 310 | 81.58 | 239 | 84.92 | 3.34 | 1.09 |
| 9:49 | 290 | 76.32 | 226 | 80.30 | 3.98 | 1.13 |
| 9:57 | 265 | 69.74 | 208 | 73.91 | 4.17 | 1.16 |
| 10:11 | 230 | 60.53 | 181 | 64.31 | 3.78 | 1.19 |
| 10:19 | 203 | 53.42 | 162 | 51.56 | 4.14 | 1.20 |
| 10:27 | 185 | 48.68 | 146 | 51.87 | 3.19 | 1.20 |
| 10:38 | 154 | 40.53 | 120 | 42.64 | 2.11 | 1.19 |
| 10:44 | 130 | 34.21 | 104 | 36.95 | 2.74 | 1.16 |
| 11:00 | 110 | 28.95 | 80 | 28.43 |  | 1.12 |
|  | 94.73 | 24.93 | 80 | 28.47 | 3.52 | 1.20 |
| 11:12 | 83 | 21.84 | 69 | 24.52 | 2.68 | 1.23 |
| 11:20 | 53 | 13.95 | 53 | 18.83 | 4.88 | 1.36 |
| 11:35 | 30 | 7.89 | 40 | 14.21 | 6.30 | 1.45 |

TABLE 3-continued

| Time | RHA left (ml) | % RHA left | ICl left to be added (ml) | % ICl left to be added | % difference | pH |
|---|---|---|---|---|---|---|
| 11:45 | 0 |  | 15 | 5.32 | 1.45 |  |
|  |  |  | 0 |  |  | 1.12 |

EXAMPLE 4

Distilled water (1348 ml) was charged to a 2 liter 4-neck round bottom flask equipped with a thermometer, pH probe, subsurface RHA inlet tube, above surface iodine chloride inlet tube, stirrer and heating mantle. A thermowatch temperature controller was provided for use in controlling the temperature of the contents of the flask. Each of the reactant solution inlet tubes was fed from a charge solution source through a Masterflex metering pump used to control the rate of addition.

The water charge was heated to a temperature of 80°-82° C. Over a two hour time period thereafter, a 0.394 g/ml iodine chloride charge solution (297.09 ml; 117.05 gms; 0.7210 moles) and a 0.213 gms/ml RHA charge solution (211.17 ml.; 45 gm; 0.2318 mole) were added to the reaction flask. Introduction of the iodine chloride solution into the reaction medium was begun just prior to the addition of RHA charge solution to make certain that the pH was sufficiently low to prevent undesirable reactions. However, immediately after introduction of iodine chloride solution was begun, addition of RHA charge solution was commenced, and addition of the two charge solutions was continued at such respective rates that a modest excess of RHA over iodine chloride prevailed through the ensuing two hour period of addition. Specifically, the respective rates of addition were controlled so that, at any instant during the addition cycle, the cumulative amount of RHA that had been added to the medium, taken as a proportion of the total ultimate charge of the substrate, exceeded the cumulative amount of iodine chloride source that had been added to the medium, taken as a proportion of the total ultimate charge of the iodine chloride source, but the arithmetic difference between such proportions was maintained in the range of 0-7%.

When approximately 10% of the RHA had been charged to the reaction flask, precipitation of iodinated product compound commenced. At the conclusion of addition of the RHA and iodinated chloride charge solution, the pH of the reaction medium was in the range of 0.7-0.8. After addition of the charge solutions was complete, the reaction mass was heated to 95° C. and maintained at that temperature for three hours. During this digest period, heat was removed and the stirrer stopped periodically to allow the taking of reaction mother liquid samples which were tested for completeness of reaction. A small amount of sodium bisulfite was added to each reaction sample prior to its analysis by high pressure liquid chromatography (HPLC). At the end of the three hour reaction period, the reaction mass was cooled to 70° C. and treated with sodium bisulfite until the reaction mother liquor gave a negative response to starch paper. The reaction mass was then cooled to 40° C. and the filter cake washed with distilled water (225 ml). The solids recovered by filtration were dried in a vacuum oven overnight at 95°-100° C. Light cream crystals having a purity of 97.6-97.8% purity were obtained in a yield of 128.66 gm. Thus the percentage yield exceeded that of the conventional process by 4.28%. HPLC analysis indicated that complete reaction had been obtained and, specifically, that the levels of di- and monoiodo species were negligible.

HPLC was run on the product without dilution and on the isolated product at a 2mg/ml level. HPLC conditions were as follows: 5 micron radial compression column, solvent A to B, 5% per minute, gradient program B, run time of 25 min., flow set 4.5 and flow 3.0.

EXAMPLE 5

Using a procedure similar to that described in Example 4, a series of iodination reactions was run at varying combinations of temperature, reaction time, net ultimate excess of iodine chloride, and post reaction treatment dosage of sodium bisulfite. The results of the runs of this series are set forth in Table 4.

TALE 4

| Exp. No. | Description | % Excess ICl | pH Digest | TIME DIGEST HRS | TEMP DIGEST °C. | gm Na BISULPHITE | % Reduction in Yield vs. Exp. #39 |
|---|---|---|---|---|---|---|---|
| 39 | Coaddition, No HCl | 3.68 | .7–.8 | 3 | 95 | 2.9 | — |
| 43 | Coaddition, No HCl | 1.70 | .7–.8 | 4½–5 | 80 | 1.5 | .35% |
| 45 | Coaddition, No HCl | .95 | .7–.8 | 6 | 80 | 1.17 | .48% |
| 47 | Coaddition, No HCl | .95 | .7–.8 | 4.5 | 90 | .85 | .47% |
| 53 | Coaddition, No HCl, 2 NH4OH Adjustments | .95 | 2.0 | 4 | 80 | .63 | — |
| 55 | Coaddition, No HCl, 2 NH4OH Adjustments | .95 | 2.0 | 3 | 80 | — | — |
| 56 | Coaddition, No HCl, Na acetate | .95 | 2.58 | 4 | 80 | .70 | — |
| 57 | Coaddition, No HCl, Na acetate | .95 | 2.40 | 4 | 80 | .43 | — |

Coaddition, buffer, digest time and temperature

These results demonstrate the high yields achieved with minimal excess iodine chloride when operating in accordance with the co-addition scheme of the process of the invention. Since operation under co-addition conditions at 3.68% excess ICl provides a 0.9–1.2% increase in the weight yield of the iodinated product as compared to operation at the same excess under standard operating conditions, it may be seen that co-addition permits the ICl excess to be reduced, for example, to 1% while still attaining a 0.6–0.9% absolute increase in product weight yield as compared to the standard process at the higher ICl excess.

From results such as those summarized above, the yield on ICl appear to be optimized at an approximately 1% net ultimate excess of ICl, a digest temperature of 80°–92° C., and a digest period of 5 to 8 hours.

EXAMPLE 6

2,4,6-triiodo-5-amino-N-methylisophthalamic acid was prepared generally in accordance with the procedure described in Example 1. The initial charge to the reaction vessel comprised water (1320 ml) and 37% hydrochloric acid (2.5 ml). The concentration of the RHA charge solution was similar to that of Example 1, but the total volume of RHA charge solution was 111.6 ml. The ICl charge solution had a strength of 0.352 g/ml and a total volume of 166.2 ml. The schedule of co-addition of charge solutions and the pH of the contents of the reaction vessel during the course of the addition are set forth in Table 5. After co-addition was completed, the mixture in the reaction vessel was heated at 95° C. for two and one-half hours, after which the pH was 0.92. By addition of 37% hydrochloric acid (20 ml), the pH was adjusted to 0.62. The reaction mixture was cooled to 70° C. and sodium bisulfite (0.4 g) was added. The product obtained by crystallization consisted of very light creamcolored crystals which were readily recovered by filtration. Yield was 65.29 g.

The ammonium salt of 2,4,6-triiodo-5-amino-N-methylisophthalamic acid (NH4.TIA) was prepared by: dissolving a portion of the iodinated product (25 g) in water (200 ml), by adding 35° Be' sodium hydroxide solution to pH of 4.5–6.0; heating the resulting solution to 60°–70° C.; adding ammonium chloride (25 g) to the solution; cooling the solution to 45° C. to crystalize out the NH4.TIA; separating the crystals from the mother liquor by filtration; and washing the filter cake with an aliquot of ammonium chloride solution (0.2 g/ml).

TABLE 5

| | An Example of 2X Dilution with Co-addition | | | | | |
|---|---|---|---|---|---|---|
| Time | mls RHA Left | % RHA Left | mls ICl Left | % ICl Left | % differ. | pH |
| 8:50 | 103 | 92.5 | 166.2 | 100 | 7.5 | 1.50 |
| 9:00 | 97 | 86.9 | 155 | 93.3 | 6.3 | 1.45 |
| 9:10 | 90 | 80.7 | 143 | 86.0 | 5.4 | 1.96 |
| 9:14 | ppt started | | | | | |
| 9:20 | 84 | 75.3 | 130 | 78.2 | 2.95 | 1.46 |
| 9:30 | 74 | 66.3 | 122 | 73.4 | 7.1 | 1.46 |
| 9:40 | 69 | 61.8 | 112 | 67.38 | 5.6 | 1.34 |
| 9:50 | 62 | 55.6 | 100 | 60.17 | 4.6 | 1.40 |
| 10:00 | 56 | 50.2 | 92 | 55.36 | 5.2 | 1.39 |
| 10:10 | 50 | 44.8 | 82 | 49.34 | 4.5 | 1.39 |
| 10:20 | 44 | 39.4 | 70 | 42.18 | 2.75 | 1.30 |
| 10:26 | 38.7 | 34.7 | 70 | 42.12 | 7.45 | 1.30 |
| 10:35 | 33 | 29.6 | 63 | 37.9 | 8.35 | 1.32 |
| 10:45 | 26.5 | 23.8 | 54 | 32.5 | 8.74 | 1.41 |
| 10:54 | 18 | 16.12 | 38 | 22.86 | 6.74 | 1.30 |
| 11:40 | stopped NH4OH (added 38 ml of 1:1 of 29.8% NH4OH over total period) | | | | | |
| 11:40 | heat to 95° C. | | | | | |
| 12:00 | T @ 95° C. - 2:30 | | | | | |

EXAMPLE 7

75% Phosphoric acid (approx. 975 lbs.) and 35° Be sodium hydroxide solution (approx. 1030 lbs.) are added slowly into a solution containing 5-amino-N,N'-bis(2,3-dihydroxypropyl)isophthalamide (approx. 780 lbs.) in a hold tank to adjust the pH to 4–4.5. The solution (approx. 670 gal.) and iodine monochloride solution (approx. 378 gal., containing 7.4 lb. moles of NaICl2) are simultaneously added into a 2000 gallon reactor which contains 470 gallons of 80° C. water, with agitation, over a period of 2–2.5 hours. To carry out this coaddition, the rates are regulated so that for each 1.7 gal. of the solution added into the reactor, approximately 1 gallon of iodine monochloride solution is added. During the additions, the reaction mixture is maintained at approximately 80° C. with hot water in the jacket of the reactor. After the additions, the mixture is stirred and heated at 77°–82° C. for 3–4 hours.

After the reaction is completed, sodium bisulfite (approx. 110 lbs.) is added to destroy excess iodine or iodine monochloride and the solution is stirred and cooled to approximately 70° C. Sodium hydroxide solution (35°Be, approximately 1620 lbs.) is added slowly at 70°–80° C. to adjust the pH to 4–7.

After seeding with 5-amino-N,N'-bis(2,3-dihydroxypropyl)-2,4 6-triiodoisophthalamide (ca. 2 lbs.), the solution is slowly cooled to about 30° C. over 3 hours. The solution is then cooled to 10°–20° C. and stirred for 15–30 hours to precipitate the product. Completeness of precipitation is determined by HPLC analysis of the liquor. The product is collected by centrifugation, washed with deionized water and dried at 45°–60° C. in a dryer until the water content is ≦1% w/w.

EXAMPLE 8

To a solution of 5-amino-N,N'-bis(2,3-dihydroxypropyl)isophthalamide (77.6 g soln.; 0.060 mol) which had been diluted with deionized water (35 ml; pH=4.2) was added 85% $H_3PO_4$ (25.2 ml, 42.9 g, 0.372 mol) followed by 50% NaOH (29.8 g, 20.0 ml, 0.372 mol). This solution was added to a flask containing 82 ml. water at a temperature of 76° C. (which had been adjusted to a pH of 1.4 with concentrated hydrochloric acid) simultaneously with an aqueous solution of iodine monochloride (85.8 ml, 186 mmol) over a period of approximately 2 hr. The schedule of coaddition of the reduced diamide and iodine monochloride solutions and the pH of the contents of the reaction flask during the course of the coaddition are set forth in the table below.

After the coaddition of the charge solutions was completed, sodium bisulfite (1.9 g) was added to quench the reaction and the pH of the solution was adjusted from 1.46 to 4.27 through the addition of a 50% NaOH solution (12 ml). The temperature increased to 88° C. After seeding with 5-amino-N,N'-bis(2,3-dihydroxypropyl)-2,4,6-triiodoisophthalamide, the solution was gradually cooled to 30° C. and the product precipitated with a yield of approximately 83.5%.

TABLE 6

| Time | ICl Remaining To Be Added (ml) | Reduced Diamide Remaining To Be Added (ml) | pH | Temp. |
| --- | --- | --- | --- | --- |
| 8:58 | 86 | 150 | 1.38 | 76° C. |
| 9:01 | 83 | 142 | 1.95 | 79° C. |
| 9:04 | 81.5 | 139 | 2.05 | 79° C. |
| 9:15 | 72 | 118 | 2.16 | 79° C. |
| 9:19 | 68 | 110 | 2.15 | 79° C. |
| 9:26 | 62.5 | 99 | 2.11 | 79° C. |
| 9:29 | 59 | 92 | 2.09 | 79° C. |
| 9:32 | 57 | 89 | 2.08 | 79° C. |
| 9:35 | 54 | 83 | 2.06 | 79° C. |
| 9:41 | 48 | 75 | 2.02 | 79° C. |
| 9:45 | 45 | 70 | 2.01 | 79° C. |
| 9:48 | 42 | 65 | 1.98 | 78° C. |
| 9:51 | 35 | 54 | 1.95 | 78° C. |
| 10:02 | 29.5 | 46 | 1.93 | 79° C. |
| 10:50 | addition complete | | | |

EXAMPLE 9

To a solution of 5-amino-N,N'-bis(2,3-dihydroxypropyl)isophthalamide (77.6 g soln; 0.060 mol) which had been diluted with water (20 ml) was added 85% $H_3PO_4$ (15.2 ml, 25.7 g; 223 mmol) followed by 50% NaOH (16.4 g, 10.9 ml, 205 mmol). This solution was added simultaneously with ICl (85.8 ml, 186 mmol) to water at a temperature of 76° C. (which had been adjusted to a pH of 1.44 with 0.05 ml HCl). The coaddition took about 2 hours and the schedule of the coaddition and the pH of the reaction medium during the course of the coaddition are shown in the table below.

After the coaddition was completed, the procedure set forth in Example 8 was followed and the desired product was obtained in a yield of approximately 80.4%.

TABLE 7

| Time | ICl Remaining To Be Added (ml) | Reduced Diamide Remaining To Be Added (ml) | pH | Temp. |
| --- | --- | --- | --- | --- |
| 8:43 | 86 | 114 | 1.44 | 76° C. |
| 8:45 | 84 | 112 | 1.57 | 75° C. |
| 8:48 | 81 | 108 | 1.39 | 75° C. |
| 8:51 | 79.5 | 104 | 1.37 | 78° C. |
| 8:54 | 78 | 101 | 1.33 | — |
| 8:56 | 76 | 98 | 1.30 | — |
| 9:02 | 71 | 91 | 1.18 | — |
| 9:08 | 66.5 | 86 | 1.01 | — |
| 9:25 | 52 | 68 | 0.98 | — |
| 9:44 | 37 | 48 | 0.86 | — |
| 9:57 | 26 | 34 | 0.83 | 76° C. |
| 10:13 | 13.5 | 17 | 0.79 | 76° C. |
| 10:39 | addition complete | | 0.68 | 76° C. |

EXAMPLE 10

To a flask containing water (100 ml) at 80° C. was added simultaneously a solution of monosodium phosphate (25 g, 181 mmol) and 5-amino-N,N'-bis(2,3-dihydroxypropyl)isophthalamide (98.4 g, 60.5 mmol) in water and a aqueous iodine monochloride solution (77.4 ml, 188 mmol). The simultaneous addition took place over a period of approximately 2 hours during which the pH of the aqueous reaction medium was maintained in the range of 0.74 to 2.00 and the temperature of the medium was maintained between 79° and 85° C.

After the coaddition was completed, the procedure set forth in Example 8 was followed and the desired product 5-amino-N,N'-bis(2,3-dihydroxypropyl)-2,4,6-triiodoisophthalamide was obtained in a yield of approximately 86%.

EXAMPLE 11

To a 500 ml flask containing water (20 ml) at a temperature of 80° C. was added simultaneously a solution containing 5-amino-N,N'-bis(2,3-dihydroxypropyl)isophthalamide (98.4 g, 60.5 mmol) containing 85% $H_3PO_4$ (43.5 g, 378 mmol) and NaOH (30 g, 375 mmol) and an aqueous iodine monochloride solution (77.4 ml). The simultaneous addition took place over a period of approximately 1.5 hours during which the pH of the reaction medium was maintained in the range 1.57 to 2.11 and the temperature of the medium was maintained at about 80° C.

After the coaddition was completed, the procedure set forth in Example 8 was followed and the desired product was obtained in a yield of 81.5%.

In view of the above, it will be seen that the several objects of the invention are achieved and other advantageous results attained.

As various changes could be made in the above process without departing from the scope of the invention, it is intended that all matter contained in the above description or shown in the accompanying drawings shall be interpreted as illustrative and not in a limiting sense.

What is claimed is:

1. In a process for the preparation of a compound selected from the group consisting of 2,4,6-triiodo-5-amino-N-alkylisophthalamic acid, salts thereof, esters thereof, 2,4,6-triiodo-5-amino-isophthalamide, 2,4,6-triiodo-5-amino-N-hydroxyalkyl-isophthalamide and 2,4,6-triiodo-5-amino-N,N'-bishydroxyalkyl-isophthalamide, comprising reaction of a substrate selected from the group consisting of 5-amino- N-alkylisophthalamic acid, salts thereof, esters, thereof, 5-amino-isophthalamide, 5-amino-N-hydroxyalkyl-isophthalamide and 5-amino-N,N'-bishydroxyalkyl-isophthalamide, with an iodine halide in an aqueous reaction medium, the improvement which comprises adding said substrate and a source of said iodine halide to said reaction medium at such respective rates that, at any instant substantially throughout the addition cycle, said substrate is present in stoichiometric excess over said iodine halide, but the arithmetic difference between the cumulative amount of said substrate that has been added to said medium at said instant, expressed as a proportion of the total ultimate charge of said substrate, and the cumulative amount of said source of iodine halide that has been added to said medium at said instant, expressed as a proportion of the total ultimate charge of said source of iodine halide, does not exceed about 10%, provided that when said substrate is 5-amino-isophthalamide, 5-amino-N-hydroxyalkyl-isophthalamide or 5-amino-N,N'-bishydroxyalkyl-isophthalamide, the cumulative amount of said iodine halide may be in stoichiometric excess of not more than about 10% over said substrate, computed on the same basis.

2. An improved process as set forth in claim 1 wherein said arithmetic difference is maintained at between about 2% and about 10%.

3. An improved process as set forth in claim 1 wherein the pH of the reaction medium at the beginning of the reaction is between about 2.5 and about 3.0.

4. An improved process as set forth in claim 1 wherein the pH of the reaction medium is maintained at not greater than about 3 during the course of the reaction.

5. An improved process as set forth in claim 4 wherein addition of said source of iodine halide is commenced just prior to the addition of said substrate to said medium so that said substrate is not exposed to a pH of greater than about 3 in said reaction medium.

6. An improved process as set forth in claim 1 wherein the concentration of said iodinated product compound does not exceed about 0.0B moles/liter in the reaction mass at the conclusion of the iodination reaction, said reaction mass comprising the combination of a liquid phase comprising said reaction medium and any solids precipitated from said medium during the course of the reaction.

7. An improved process as set forth in claim 6 where the concentration of said iodinated product compound does not exceed about 0.08 moles/liter in the reaction mass at any time during the iodination reaction cycle.

8. An improved process as set forth in claim 7 wherein the sum of the amounts of said substrate and said iodinated product compound added to said medium does not exceed about 0.08 moles/liter in the reaction mass at any time during said reaction cycle.

9. An improved process as set forth in claims 6 wherein the reaction is carried out in the presence of an alkaline buffer composition, the proportion of said alkaline buffer composition being sufficient so that the pH of said reaction medium is maintained at between about 0 and about 3 during the course of the reaction.

10. An improved process as set forth in claim 9 wherein said buffer composition is selected from the group consisting of alkali metal acetates, ammonium hydroxide, alkali metal phosphates and alkali metal citrates.

11. An improved process as set forth in claim 10 wherein said buffer composition comprises an alkali metal acetate.

12. An improved process as set forth in claim 11 wherein said alkali metal acetate is produced in situ by adding an alkali metal hydroxide and glacial acetic acid to said reaction medium.

13. An improved process as set forth in claim 12 wherein said alkali metal hydroxide is added in the form of an aqueous solution thereof that contains between about 25% and about 70% by weight of said alkali metal hydroxide.

14. An improved process as set forth in claim 11 wherein a substrate charge solution comprising an aqueous solution of said substrate and an iodine halide charge solution comprising an aqueous solution containing a source of said iodine halide are simultaneously added to and mixed in a reaction vessel, said alkali metal acetate being provided by introducing an alkali metal hydroxide and glacial acetic acid into said substrate charge solution before mixing thereof with said iodine halide charge solution.

15. An improved process as set forth in claim 14 wherein said alkali metal hydroxide is introduced in the form of an aqueous solution thereof that contains between about 25% and about 70% by weight of said alkali metal hydroxide.

16. An improved process as set forth in claim 10 wherein said buffer comprises ammonium hydroxide.

17. An improved process as set forth in claim 16 wherein a substrate charge solution comprising an aqueous solution of said substrate and an iodine halide charge solution comprising an aqueous solution containing a source of said iodine halide are simultaneously added to and mixed in a reaction vessel, ammonium hydroxide being incorporated into said substrate charge solution before mixing thereof with said iodine halide charge solution.

18. An improved process as set forth in claim 9 wherein the total charge of said substrate and the total charge of said iodine halide added to said reaction medium over the course of the reaction are in substantial stoichiometric equivalence.

19. An improved process as set forth in claim 9 wherein the pH of the reaction medium at the beginning of the reaction period is between about 2.5 and about 3.0.

20. An improved process as set forth in claim 1 wherein said compound is 2,4,6-triiodo-5-amino-N-alkylisophthalamic acid.

21. An improved process as set forth in claim 1 wherein said compound is 5-amino-N,N'-bis(2,3-dihydroxypropyl)-2,4,6-triiodoisophthalamide.

22. In a process for the preparation of a compound selected from the group consisting of 2,4,6-triiodo-5-amino-N-alkylisophthalamic acid, salts thereof, esters thereof, 2,4,6-triiodo-5-amino-isophthalamide, 2,4,6-triiodo-5-amino-N-hydroxyalkyl-isophthalamide and 2,4,6-triiodo-5-amino-N,N'bishydroxyalkyl-isophthalamide, comprising reaction of a substrate selected from the group consisting of 5-amino-N-alkylisophthalamic acid, salts thereof, esters thereof, 5-amino-isophthalamide, 5-amino-N-hydroxyalkyl-isophthalamide and 5-amino-N,N'-bishydroxyalkyl-isophthalamide, with an iodine halide in an aqueous reaction medium, the improvement which comprises carrying out the reaction in the presence of an alkaline buffer composition, the proportion of said alkaline buffer composition being sufficient so that the PH of said reaction medium is maintained at between about 0 and about 3 during the course of the reaction.

23. An improved process as set forth in claim 22 wherein said buffer composition is selected from the group consisting of alkali metal acetates, ammonium hydroxide, alkali metal phosphates and alkali metal citrates.

24. An improved process as set forth in claim 23 wherein said buffer composition comprises an alkali metal acetate.

25. An improved process as set forth in claim 24 wherein said alkali metal acetate is produced in situ by adding an alkali metal hydroxide and glacial acetic acid to said reaction medium.

26. An improved process as set forth in claim 25 wherein said alkali metal hydroxide is added in the form of an aqueous solution thereof that contains between about 25% and about 70% by weight of said alkali metal hydroxide.

27. An improved process as set forth in claim 24 wherein a substrate charge solution comprising an aqueous solution of said substrate and an iodine halide charge solution comprising an aqueous solution containing a source of said iodine halide are simultaneously added to and mixed in a reaction vessel, said alkali metal acetate being provided by introducing an alkali metal hydroxide and glacial acetic acid into said substrate charge solution before mixing thereof with said iodine halide charge solution.

28. An improved process as set forth in claim 27 wherein said alkali metal hydroxide is introduced in the form of an aqueous solution thereof that contains between about 25% and about 70% by weight of said alkali metal hydroxide.

29. An improved process as set forth in claim 22 wherein said substrate and a source of said iodine halide are added to said reaction medium in substantial stoichiometric equivalence and the reaction is carried out with substantially stoichiometrically equivalent amounts of substrate and iodine halide in the reaction medium.

30. An improved process as set forth in claim 29 wherein said buffer composition is selected from the group consisting of alkali metal acetates, ammonium hydroxide, alkali metal phosphates and alkali metal citrates.

31. An improved process as set forth in claim 30 wherein said buffer composition comprises an alkali metal acetate.

32. An improved process as set forth in claim 31 wherein said alkali metal acetate is produced in situ by adding an alkali metal hydroxide and glacial acetic acid to said reaction medium.

33. An improved process as set forth in claim 31 wherein a substrate charge solution comprising an aqueous solution of said substrate and an iodine halide charge solution comprising an aqueous solution containing said source of iodine halide are simultaneously added to and mixed in a reaction vessel, said alkali metal acetate being provided by introducing an alkali metal hydroxide and glacial acetic acid into said substrate charge solution before mixing thereof with said iodine halide charge solution.

34. An improved process as set forth in claim 33 wherein said alkali metal hydroxide is introduced in the form of an aqueous solution thereof that contains between about 25% and about 70% by weight of said alkali metal hydroxide.

35. An improved process as set forth in claim 22 wherein a substrate charge solution comprising an aqueous solution of said substrate and an iodine halide charge solution comprising an aqueous solution containing a source of said iodine halide are simultaneously added to and mixed in a reaction vessel, and thereafter the resulting mixture is maintained at a temperature of between about 90° and about 100° C. to complete the triiodination of the substrate.

36. An improved process as set forth in claim 35 wherein an initial water charge is introduced into a reaction vessel provided with an agitator, after said water charge has been introduced said substrate charge solution and said iodine halide charge solution are simultaneously added to the reactor and the contents of the reactor are stirred with the agitator to provide a substantially homogeneous mixture, and thereafter the resulting mixture is heated to complete the triiodination of the substrate.

37. An improved process as set forth in claim 35 wherein said substrate charge solution contains between about 0.1 and about 0.3 moles per liter of said substrate.

38. An improved process as set forth in claim 37 wherein said iodine halide charge solution contains between about 0.2 and about 0.5 equivalents per liter of said source of iodine halide.

39. An improved process as set forth in claim 22 wherein said compound is 2,4,6-triiodo-5-amino-N-alkylisophthalamic acid.

40. An improved process as set forth in claim 22 wherein said compound is 5-amino-N,N'-bis(2,3-dihydroxypropyl)-2,4,6-triiodoisophthalamide.

41. In a process for the preparation of a compound selected from the group consisting of 2,4,6-triiodo-5-amino-N-alkylisophthalamic acid, salts thereof, esters thereof, 2,4,6-triiodo-5-amino-isophthalamide, 2,4,6-triiodo-5-amino-N-hydroxyalkyl-isophthalamide and 2,4,6-triiodo-5-amino-N,N'-bishydroxyalkyl-isophthalamide, comprising reaction of a substrate selected from the group consisting of 5-amino-N-alkylisophthalamic acid, salts thereof, esters thereof, 5-amino-isophthalamide, 5-amino-N-hydroxyalkyl-isophthalamide and 5-amino-N,N'-bishydroxyalkyl-isophthalamide, with an iodine halide in an aqueous reaction medium, the improvement which comprises adding said substrate and a source of said iodine halide to said reaction medium in the presence of an alkaline buffer composition and at such respective rates that, at any instant substantially throughout the addition cycle, said substrate is present in stoichiometric excess over said iodine halide, but the arithmetic difference between the cumulative amount of said substrate that has been added to said medium at said instant, expressed as a proportion of the total ultimate charge of said substrate, and the cumulative amount of said source of iodine halide that has been added to said medium at said instant, expressed as a proportion of the total ultimate charge of said source of iodine halide, does not exceed about 10%, the proportion of said alkaline buffer composition being sufficient so that the pH of said reaction medium is maintained at between about 0 and about 3 during the course of the reaction, provided that when said substrate is 5-amino-isophthalamide, 5-amino-N-hydroxyalkyl-isophthalamide or 5-amino-N,N'-bishydroxyalkyl-isophthalamide, the cumulative amount of said iodine halide may be in stoichiometric excess of not more than about 10% over said substrate, computed on the same basis.

42. An improved process as set forth in claim 41 wherein said buffer composition is selected from the group consisting of alkali metal acetates, ammonium hydroxide, alkali metal phosphates and alkali metal citrates.

43. An improved process as set forth in claim 41 wherein said compound is 2,4,6-triiodo-5-amino-N-alkylisophthalamic acid.

44. An improved process as set forth in claim 41 wherein said compound is 5-amino-N,N'-bis(2,3-dihydroxypropyl)-2,4,6-triiodoisophthalamide.

45. In a process for the preparation of an iodinated product compound selected from the group consisting of 2,4,6-triiodo-5-amino-N-alkylisophthalamic acid, salts thereof and esters thereof, comprising reaction of a substrate selected from the group consisting of 5-amino-N-alkylisophthalamic acid, salts thereof and esters thereof with an iodine halide in an aqueous reaction medium, the improvement which comprises maintaining a sufficient proportion of water in the reaction medium so that the concentration of said iodinated product compound does not exceed about 0.04 moles/liter in the reaction mass at the conclusion of the iodination reaction, said reaction mass comprising the combination of a liquid phase comprising said medium and any solids that precipitate during the course of the reaction.

46. An improved process as set forth in claim 45 wherein the concentration of said iodinated product compound does not exceed about 0.08 moles/liter in the reaction mass at any time during the iodination reaction cycle.

47. An improved process as set forth in claim 46 wherein the sum of the amounts of said substrate and said iodinated product compound in said medium does not exceed about 0.08 moles/liter in the reaction mass at any time during said reaction cycle.

48. A process for the preparation of an iodinated compound selected from the group consisting of 2,4,6-triiodo-5-amino-N-alkylisophthalamic acid, salts thereof and esters thereof, the process comprising:

adding to a reaction vessel an aqueous substrate solution and an aqueous iodine halide charge solution, said substrate solution containing a substrate selected from the group consisting of 5-amino-N-alkylisophthalamic acid, salts thereof, and esters thereof, and said iodine halide charge solution containing a source of iodine halide; and reacting said substrate with said source of iodine halide in an aqueous medium in said vessel to produce said iodinated compound;

the respective rates of addition of said substrate solution and said iodine halide charge solution to said vessel being such that, at any instant substantially throughout the addition cycle, said substrate is present in excess over said iodine halide, but the arithmetic difference between the cumulative amount of said substrate that has been added to said medium, expressed as a proportion of the total ultimate charge of said substrate, and the cumulative amount of said iodine halide source that has been added to said medium at said instant, expressed as a proportion of the total ultimate charge of said source of iodine halide, does not exceed 5%, the reaction being carried out in the presence of an alkaline buffer composition, the proportion of said alkaline buffer composition being sufficient so that the pH of said reaction medium is maintained at between about 0 and about 3 during the course of the reaction, the pH of the reaction medium at the beginning of the reaction is between about 2.5 and about 3.0, and the concentration of said iodinated product compound not exceeding about 0.08 moles/liter in the reaction mass at the conclusion of the iodination reaction, said reaction mass comprising the combination of a liquid phase comprising said reaction medium and any solids precipitated from said medium during the course of the reaction.

49. A process for the preparation of 5-amino-N,N'-bis(2,3-dihydroxypropyl)-2,4,6-triiodoisophthalamide comprising the simultaneous coaddition to an aqueous reaction medium of an aqueous solution containing 5-amino-N,N'-bis(2,3-dihydroxypropyl)isophthalamide and monosodium phosphate and an aqueous solution of iodine monochloride, said aqueous reaction medium being maintained at a temperature within the range 75°–85° C. and at a pH within the range 0.5 to 2.5 during said simultaneous coaddition, and continuing said simultaneous coaddition for a period of approximately 2 to 2.5 hours.

* * * * *